United States Patent [19]

Levy

[11] Patent Number: 4,773,855
[45] Date of Patent: Sep. 27, 1988

[54] ENDODONTIC APPLIANCE

[76] Inventor: Guy Levy, 49, rue Croix de Regnier, F-13004 Marseille, France

[21] Appl. No.: 916,731

[22] Filed: Oct. 8, 1986

Related U.S. Application Data

[62] Division of Ser. No. 723,625, Apr. 15, 1985, Pat. No. 4,629,426.

[30] Foreign Application Priority Data

Apr. 20, 1984 [FR] France ................................ 84 06446

[51] Int. Cl.⁴ ................................................ A01C 5/02
[52] U.S. Cl. .................................... 433/102; 433/122; 433/118
[58] Field of Search ......................... 433/122, 118, 102

[56] References Cited

U.S. PATENT DOCUMENTS 2,135,933 11/1938 Blair ...................................... 433/122
4,299,571 11/1981 McSpadden ........................ 453/102

Primary Examiner—Robert Peshock
Attorney, Agent, or Firm—Spensley Horn Jubas & Lubitz

[57] ABSTRACT

Drive head for an endodontic treatment instrument composed of a support body provided with a passage, an instrument support member having a longitudinal axis and mounted in the passage for movement relative to the body in the direction of the longitudinal axis, and drive components coupled to the instrument support member for inparting to the instrument support member alternating movements in the direction of the longitudinal axis, said instrument support member supports an andodontic treatment instrument in a manner to cause the instrument to move with the support in the direction of said longitudinal axis and to have a freedom of rotation about the longitudinal axis and relative to the support body and/or to cause the alternating movements in the direction of the longitudinal axis to have a variable amplitude.

10 Claims, 3 Drawing Sheets

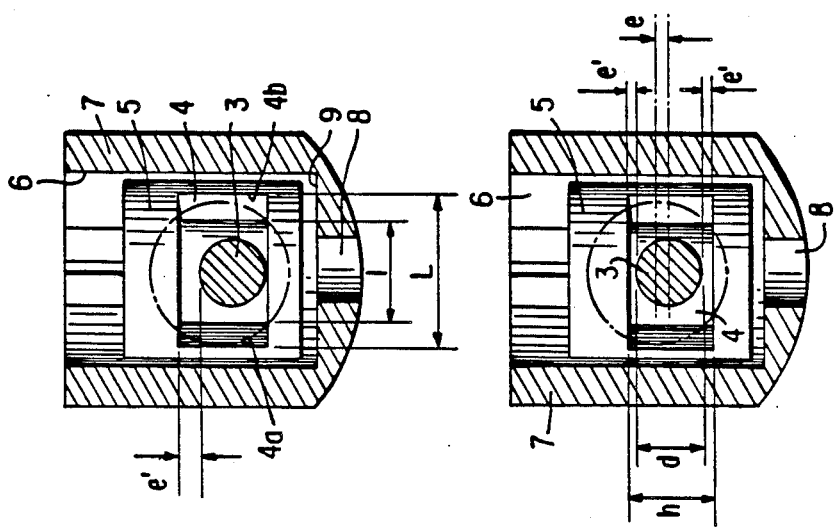
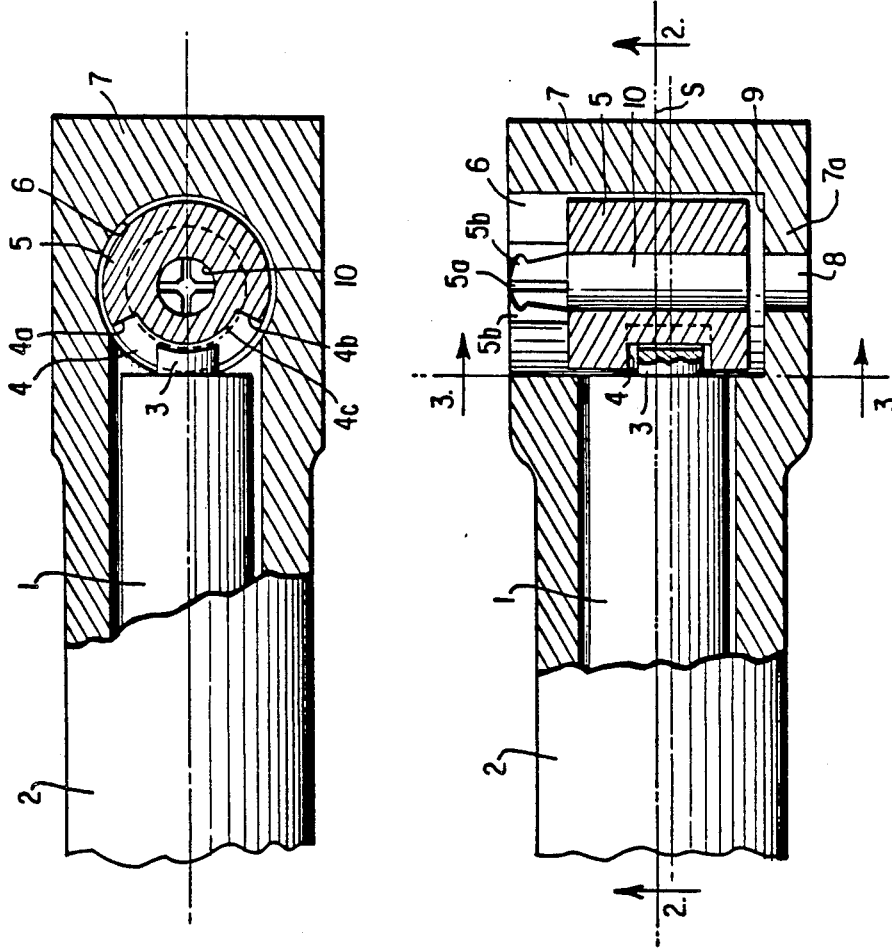

ENDODONTIC APPLIANCE

This is a division of application Ser. No. 723,625 filed Apr. 15, 1985, and now U.S. Pat. No. 4,629,426 issued 12/16/86.

BACKGROUND OF THE INVENTION

The present invention relates to an endodontic appliance, and in particular a device for driving endodontic instruments. More specifically, the invention is directed to a drive device in the form of an end piece, or contra-angle, for mechanically driving the instruments utilized in the various steps of an endodontic treatment.

Endodontic treatments, commonly known as root canal treatments, generally consist of three successive operations:

catheterization, which effects an initial penetration into the root canal in order to provide an initial small diameter passage to around 0.5 mm of the apex, and to prepare the canal for the second operation;

creation of the final form of the passage in the root canal, in order to scrape out the canal along its entire length and to form a uniform bore facilitating the third operation;

closing of the canal in order to fill the empty space created during the first and second operations.

These operations constitute interventions which are delicate, notably because a tooth canal can have configurations which are extremely varied, depending on the type of tooth involved, i.e. canine, incisor, molar, second molar, etc., and on the pathological and physiological processes to which the tooth has previously been subjected. These variations relate to the longitudinal configuration of the canal as well as to its transverse cross section.

On the other hand, catheterization and formation of the canal are effected with relatively thin instruments which are highly exposed to the risk of breakage or permanent deformation.

Presently, there is no endodontic apparatus which permits the totality of the three above-mentioned operations to be effectuated mechanically without some manual interventions, so that these operations are presently performed manually or with the aid of various types of apparatus each constructed to perform only one of the operations.

There exist forms of apparatus for mechanically performing the catheterization operation but, this constituting a particularly delicate intervention, very few mechanized solutions have been proposed to date and the solutions which have been proposed possess significant drawbacks.

For example, devices for driving catheterization instruments, such as a "MMC" file or a Kerr file, to cause them to undergo alternating movements in the longitudinal direction are known. A filing performed with the aid of such devices is effective for a straight canal, but it is dangerous, since it creates recesses in the side walls of the canal, in the case of canals which are curved or in the presence of a stricture in the canal.

Devices permitting the driving of catheterization instruments to undergo alternating partial rotation movements are also known. While this is effective in the case of a canal having a round cross section, such a movement becomes exceedingly dangerous if parietal contact should occur, or if the tip of the instrument should become blocked, leading to a type of "unkinking" of the instrument. This "unkinking" constitutes a partial untwisting of the spiral crest of the instrument, and is often produced by torsion of a steel file of rectangular cross section. In addition, such blockage can lead to breakage of the file, which is extremely troublesome.

Because of the drawbacks of existing mechanical devices, practitioners most often prefer to perform this delicate intervention manually with catheterization instruments.

There also exist devices for performing the second operation of placing the canal in the desired form, which operation is intended to increase the volume of the radicular canal, in a harmonious manner, while removing the pulpy parenchyma.

Certain of these devices permit the working instrument (K file, H file, etc.) to be driven to undergo alternating partial rotational movements. A drawback of this type of drive is that it leads to a significant modification of the apical tier, or portion, in the case of curved canals, as a result of a sweeping by the free end of the instrument over a large surface area. Another drawback of devices operating according to this principle is the frequent breakage of the instruments as a result of blockage of their tip.

Any breakage of such an instrument in the tooth canal is extremely troublesome because of the substantial difficulty of extracting the broken part.

Other known devices operate to impart alternating longitudinal movements to the working instrument. These devices are disadvantageous because the amplitude of the movements which they produce is constant, and therefore sometimes too long and sometimes too short for the existing situation. When the movement is too long, there is the danger that the tip of the instrument will abut against the canal wall and then break upon encountering a bend in the canal wall, even if the bend is slight. When the amplitude of the movements is too short for the given situation, the working effectiveness of the instrument is reduced.

The above-mentioned drawbacks resulting from the utilization of known devices for giving the canal its final form have as a result that practitioners prefer most often to also perform this operation manually.

Finally, there does not exist to date any device for mechanizing the third operation of closing the canal passage by compaction of gutta-percha, which is the most commonly used and reliable material, so that this third operation is, to date, always performed manually.

SUMMARY OF THE INVENTION

It is an object of the present invention to eliminate the drawbacks of known devices for mechanically performing the operations of catheterization and formation of the canal passage in connection with an endodontic treatment.

Another object of the invention is to enable these operations to be mechanized.

Another object of the invention is to permit all of the operations associated with such an endodontic procedure, including closing of the canal passage, to be mechanized.

A further object of the invention is to simplify all of these operations.

Another object of the invention is to reduce the time needed to perform such operations.

Yet another object of the invention is to reduce the risks to patients during the performance of these operations, and in particular to reduce the risks of breakage of an instrument in a tooth canal.

The above and other objects of the invention are achieved by a novel drive head for an endodontic treatment instrument, comprising: a support body provided with a passage; instrument support means having a longitudinal axis and mounted in the passage for movement relative to the body in the direction of the longitudinal axis; and drive means coupled to the instrument support means for imparting to the instrument support means alternating movements in the direction of the longitudinal axis, the instrument support means constituting means for supporting an endodontic treatment instrument in a manner to cause the instrument to move with the body in the direction of said longitudinal axis and to have a freedom of rotation about the longitudinal axis and relative to the support body.

The objects according to the invention are additionally achieved by a novel drive head for an endodontic treatment instrument, comprising: a support body provided with a passage; instrument support means having a longitudinal axis and mounted in the passage for movement relative to the body in the direction of the longitudinal axis; and drive means coupled to the instrument support means for imparting to the instrument support means alternating movements having an amplitude which is variable in the direction of the longitudinal axis, the instrument support means constituting means for supporting an endodontic treatment instrument in a manner to cause the instrument to move with the body in the direction of the longitudinal axis.

The drive head according to the present invention, which can be in the form of an end piece, or contra-angle, offers a number of advantages and valuable possibilities.

It permits, in the first place, all of the operations associated with an endodontic procedure to be mechanized, the operations in question including the catheterization, placement of the canal passage in the desired final form, and closing the canal by introduction and compression of gutta-percha.

In addition, the invention offers advantages in connection with each of the operations of such a procedure.

During catheterization, the file mounted on the drive head according to the invention is given a vibratory movement resulting from the high frequency alternating longitudinal movement imparted thereto by the drive means of the instrument-carrying core. Upon encountering an obstacle, such as an abrupt reduction in the cross section of the canal or other obstacle, or a bend in the canal, the file is permitted to rotate as a result of contact between the inclined crest of the file and the adjacent parietal surface, this movement being permitted by mounting of the core with a certain freedom of rotation and/or by mounting of the instrument, i.e. the file, in the core to permit such rotation.

Upon encountering an obstacle, the amplitude of the longitudinal movement of the catheterization instrument is reduced to a small value which facilitates further progression of the instrument through the canal, permitting in particular an easy traversal of the obstacles and bends in the canal, without causing the tip of the instrument to abut against the canal wall or to begin creating a false canal, and without experiencing blockage forces, the instrument thus being permitted to follow the actual path of the canal perfectly. These operations are further facilitated when the instrument is permitted a certain freedom of rotation under the influence of forces produced by contact with the canal walls.

During the operation of giving the canal its final form, the drive head according to the invention permits a large amplitude filing movement to be effected when the resistance of the walls of the canal to the file is low, and a filing motion of small amplitude when the parietal resistance increases. This action significantly reduces the danger of the tip of the file abutting against the canal wall. However, when the file is driven at high speeds, the amplitude of its alternating longitudinal movements is equally reduced.

It might be noted at this point that the operation of the device according to the present invention is such that the amplitude of the longitudinal movement of the instrument performing the particular operation is variable as a function of the resistance encountered by the instrument and as a function of the speed at which the core is being displaced. These variations will occur, of course, between the minimum and maximum displacement values dictated by the dimensions of the drive mechanism. Variations in the amplitude of displacement of the instrument with variations in drive speed are due primarily to the inertia of the moving assembly, composed of the instrument and the core.

For the third operation of an endodontic procedure, the closing of the canal, for example by compaction of gutta-percha, it is possible to mount, on the drive head according to the present invention, a condenser, or compactor, of the type presently manipulated by hand, with the shaft of that instrument being constructed to permit its removable insertion into the core of the drive head. When this operation is performed according to the invention, the free end of the condenser is able to heat the gutta-percha by friction, to thereby render the filling material more malleable. As a result, the possibility of leaving air spaces is substantially reduced and complete filling of the canal with a homogeneous mass of filling material is facilitated.

BRIEF DESCRIPTION OF THE DRAWING

FIG. 1 is a side elevational view, partly in cross section, of a drive head for endodontic intruments according to a preferred embodiment of the invention. The plane of FIG. 1 contains the axis of the mobile instrument-holding core of the drive head.

FIG. 2 is a bottom view, partly in cross section, taken along the line 2—2 of FIG. 1.

FIG. 3 is a cross-sectional view taken along the line 3—3 of FIG. 1.

FIG. 4 is a cross-sectional view similar to that of FIG. 3, particularly illustrating the mechanism which permits the amplitude of movement of the core to be varied and which gives the core and an instrument connected thereto a limited freedom of rotation.

DESCRIPTION OF THE PREFERRED EMBODIMENTS

Figure 5:
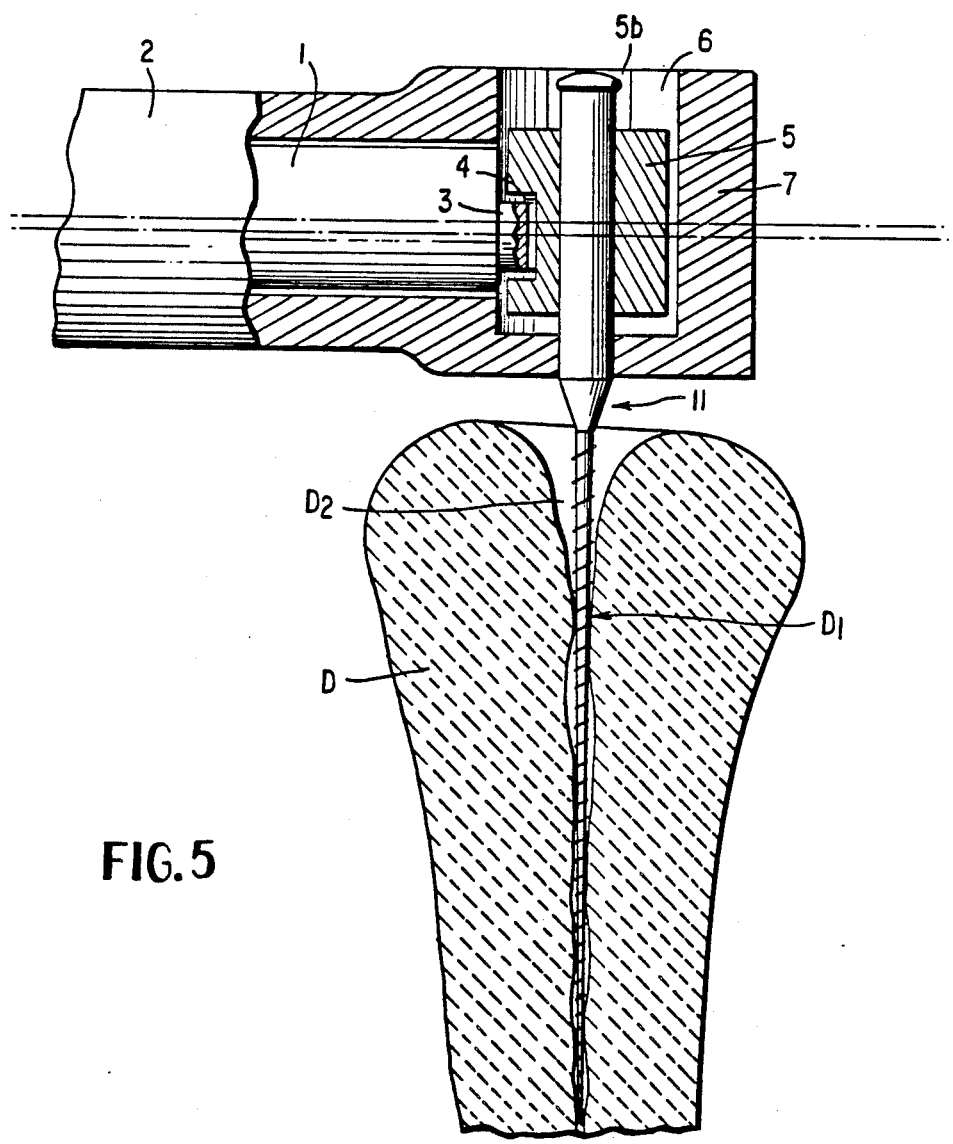
FIG. 5 is a view similar to that of FIG. 1 carrying an instrument which is in the process of penetrating a tooth canal.

A drive head according to the present invention can advantageously be constituted by a contra-angle head, or end piece. Such a device includes conventional elements which, not forming part of the present invention, are not illustrated and will not be described in detail.

Referring to FIGS. 1-5 as a group, the device according to the invention includes a cylindrical metal housing 2 provided with a cylindrical bore in which is disposed a rotary shaft 1 whose exterior end (not shown) is constructed to be coupled to an appropriate transmission selected to rotate shaft 1 at the desired speed. For example, such a transmission forms a part of an electrical tower employed by dentists and dental surgeons. Shaft 1 can be associated with a speed reducer also forming part of the end piece to enable the desired rotation speed to be imparted to shaft 1 by the connected transmission. Housing 2 can be equipped with a conventional grease joint constituting a low friction slide bearing for shaft 1.

The output end of shaft 1 is equipped with an eccentric element 3 constituted by a pin, which, in the illustrated embodiment, has a circular cross section, but can also have an oval or elliptical cross section.

Shaft 1 and eccentric 3 may have, by way of example, diameters of 8 mm and 3 mm, respectively. The distance between the center of rotation of shaft 1 and the geometric center of eccentric 3 constitutes the eccentricity e in the rotational movement of eccentric 3. The external face of eccentric 3 can be flat, but is preferably concave, for reasons to be explained below.

Eccentric 3 is housed in a groove or slideway 4 formed in the side face of a cylindrical core 5 movably held in a cylindrical cavity 6 of a body 7 forming the free end of the end piece. Body 7 can be integral with housing 2.

The longitudinal axis of cavity 6 is preferably perpendicular to the axis of housing 2 and the axis of rotation of shaft, and body 7 has a bottom wall 7a provided with a central passage 8, preferably having a circular form. The internal surface of bottom wall 7a can advantageously be provided with a coating 9 of a plastic material, such as polyfluorethenes, one example being the material sold under the trademark Teflon. This coating serves to damp vibrations.

The upper end of cavity 6, corresponding to the upper surface of body 7, can remain open or can be closed by a removable cover.

Movable core 5 has a generally cylindrical form and is housed in cavity 6 to be capable of sliding axially therein. The wall of cavity 6 and the cylindrical surface of core 5 are formed to establish a low friction sliding contact. Core 5 can be dimensioned to permit a certain amount of lateral play in cavity 6.

In further accordance with the invention, core 5 is mounted to have a certain degree of freedom of rotation in cavity 6. However, according to alternative embodiments of the invention, the wall of cavity 6 and core 5 can be constructed so that core 5 does not have freedom of rotation. However, in this case, core 5 is constructed to retain an instrument, i.e. a file, in a manner to give the instrument freedom of rotation relative to core 5.

In order to support an instrument, core 5 is provided with an axially extending recess 10 aligned with the axis of passage 8. Moreover, core 5 is provided with suitable means for releasably but securely holding in recess 10 the shank of an endodontic instrument. In the illustrated embodiment, these means are composed of axially extending fingers 5b separated by axial grooves 5a and integral with the body of core 5. In the illustrated embodiment, and as is particularly evident from FIG. 2, four such fingers are provided. Fingers 5b may be integral with the body of core 5 and the body can be constructed of a suitable steel which, in conjunction with selection of a suitable thickness for the walls of fingers 5b, will give fingers 5b the ability to be flexed outwardly during insertion of the shank of an instrument. At their upper ends, fingers 5b are provided with inwardly directed flanges which serve to retain the top of such shank. The inner surfaces of fingers 5b are provided, immediately below the inwardly directed flanges, with arcuate recesses, as shown in FIG. 1, for retaining a correspondingly shaped portion at the top of the instrument shank. Extending downwardly from these recesses, the inner walls of fingers 5b diverge downwardly to the body of core 5.

When the shank of an instrument having an enlarged head corresponding to the recesses near the top of fingers 5b is inserted into the end piece from below, the shank head deflects fingers 5b radially outwardly until the head comes to rest in the recesses near the upper ends of fingers 5b. The instrument will then be securely held in place by the spring action of fingers 5b until the instrument is released by means of a special tool which can be inserted into the circular opening enclosed by the flanges at the top of fingers 5b, this opening being apparent from FIG. 2.

Fingers 5b can be dimensioned, and/or given a spring constant, sufficient to prevent an instrument from rotating relative to core 5. Alternatively, particularly if core 5 does not have any freedom of rotation in recess 6, fingers 5b can be constructed to permit an instrument to have a certain freedom of rotation relative to core 5.

The outer surface of core 5 is provided with a groove or slideway 4 which, in the illustrated embodiment, extends circumferentially beyond the region of action of eccentric 3. As is apparent from FIGS. 3 and 4, the height of groove 4, i.e. the dimension parallel to the axis of body 5, has a value h which exceeds the diameter d of eccentric 3 by an amount e' which constitutes the play of eccentric 3 in groove 4, eccentric 3 projecting into groove 4 so that when shaft 1 rotates, eccentric 3 imparts an oscillatory longitudinal movement to core 5.

If eccentric 3 has an oval or elliptical shape, then the dimension e' is measured relative to the largest cross-sectional dimension, or axis of symmetry, of eccentric 3.

As will be apparent, the range of longitudinal movement of core 5 in response to rotation of shaft 1 will depend on the values of e and e'. The smallest value for the longitudinal movement will exist when the instrument mounted in core 5 is encountering a high level of resistance, so that core 5 is displaced longitudinally only when the upper or lower wall of groove 4 is being contacted by eccentric 3. The longitudinal displacement of core 5 will have its largest amplitude when the instrument which it carries is encountering minimal resistance. In this case, as a result of the inertia possessed by core 5 and the instrument connected thereto, the assembly of these parts will continue to move in a given direction after the direction of longitudinal displacement of eccentric 3 has been reversed and until the then trailing horizontal wall of core 5 has come into contact with eccentric 3.

According to the invention, the dimensions e and e' are given values which assure that the minimum displacement amplitude of core 5 will correspond to the pitch of the spiral crest of an associated file. For example, the files currently employed for effecting catheterization and creation of the final shape of a root canal have a spiral crest pitch of the order of 0.5 mm. According to preferred embodiments of the invention, the values of e and e' are selected to permit the amplitude of the longitudinal displacement of core 5 to vary between a minimum value of 0.5 mm and a maximum value of 1.25 mm.

Thus, when shaft 1 is placed into rotation, eccentric 3 is caused to undergo an oscillatory movement having a component parallel to the axis of core 5. As a result of this movement, eccentric 3 strikes the upper and lower horizontal walls of groove 4 alternatingly to impart a corresponding oscillatory movement to core 5 in the direction of its axis, while core 5 is guided by the wall of recess 6.

As noted above, the inertia, or momentum, of core 5 gives it a tendency to have a maximum longitudinal displacement amplitude. However, this amplitude will be reduced as a function of the resistance encountered by the instrument carried by core 5. In addition, as the rate of rotation of shaft 1 increases, this will also tend to reduce the amplitude of longitudinal displacement of the core.

Ihe relation between the amplitde of displacement core 5 and the resistance encountered by an instrument carried by that core produces a number of advantageous results, which have a particularly beneficial effect during the second operation of an endodontic procedure. When, during this operation, the instrument being employed encounters a significant parietal resistance, the operation can continue most effectively if the amplitude of the longitudinal displacement of the instrument is reduced to a low value. However, the minimum displacement value should not be less than, or substantially less than, the pitch of the spiral crest of the instrument. When the amplitude of displacement of the instrument is reduced to this value upon encountering a substantial resistance, the danger of breakage or damage to the instrument is substantially reduced. On the other hand, when the resistance encountered by the instrument is low, it is preferable to cause the instrument, i.e. the file, to undergo a longitudinal displacement having a large amplitude.

In addition, as has been noted above, embodiments of the present invention are constructed to permit an instrument to have at least a certain freedom of rotation. In the illustrated embodiment, when the instrument is prevented from rotating relative to core 5, the amplitude of the freedom of rotation is limited by vertical side walls 4a and 4b of groove 4 giving the groove a circumferential length L which is substantially greater than the circumferential length of the region 1 traversed by eccentric 3 during a complete cycle of rotation. In the illustrated embodiment, the freedom of rotation of core 5 is limited by walls 4a and 4b which are spaced apart by an angular distance of less than 180°.

On the other hand, in order to facilitate rotational movements of core 5, the bottom 4c of groove 4 preferably has a rounded, e.g. cylindrical, form.

As a result of this arrangement, and referring to FIG. 5, when an endodontic instrument such as a catheterization file 11 mounted in core 5 encounters an obstacle $D_1$ or a bend, as instrument 11 is penetrating tooth canal $D_2$ of tooth D, the inclination of the spiral crest at the outer surface of file 11 interacts with the tooth canal to produce a rotation of file 11 about its axis. As noted above, this can involve a rotation of file 11 together with core 5 or relative thereto. This occurs as the spiral crest bites into the tooth dentine. This rotational movement which is, in effect, guided by the spiral crest of file 11, combined with the small amplitude longitudinal movement of file 11, greatly facilitates movement of file 11 past obstacle $D_1$ or a bend.

As noted above, in order to permit the spiral crest to be fully active, the minimum amplitude of longitudinal displacement of file 11 should not be inferior to the pitch of the spiral crest, which is typically 0.5 mm. It is believed that if the longitudinal displacement of such a file is permitted to drop below 0.33 mm, the file will no longer perform any effective operation, and will be unable to effect further removal of material from the canal wall.

Depending on the characterictics of the file to be employed, the number of turns per millimeter of its crest and the inclination of the crest relative to the length of a file, the minimum desirable amplitude of longitudinal displacement of such a file can, of course, be greater than or less than the numerical values mentioned above. Similarly, the maximum desirable amplitude of longitudinal displacement can vary in dependence on the characteristic of the files employed.

Figure 7:
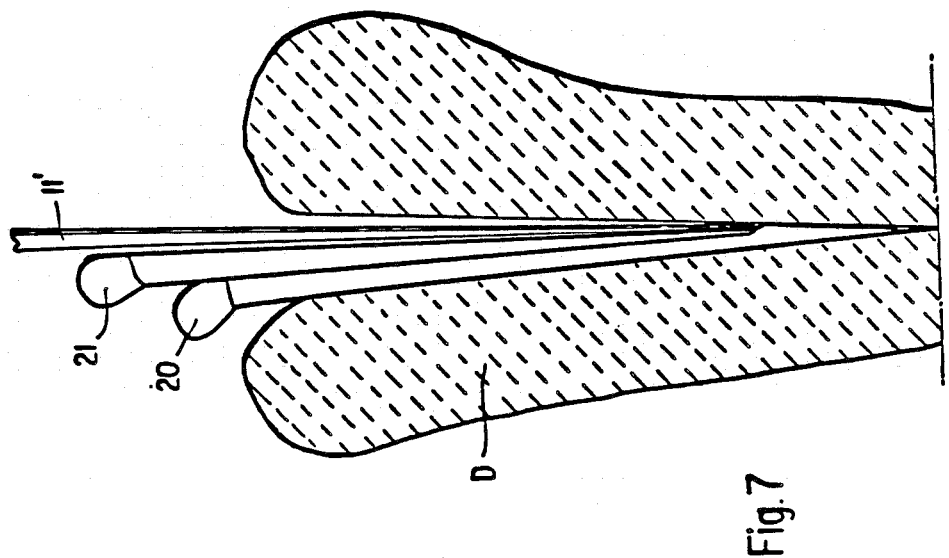
FIGS. 6 and 7 are cross-sectional detail views illustrating successive stages in the third operation of an endodontic procedure, employing the device according to the present invention.
Figure 6:
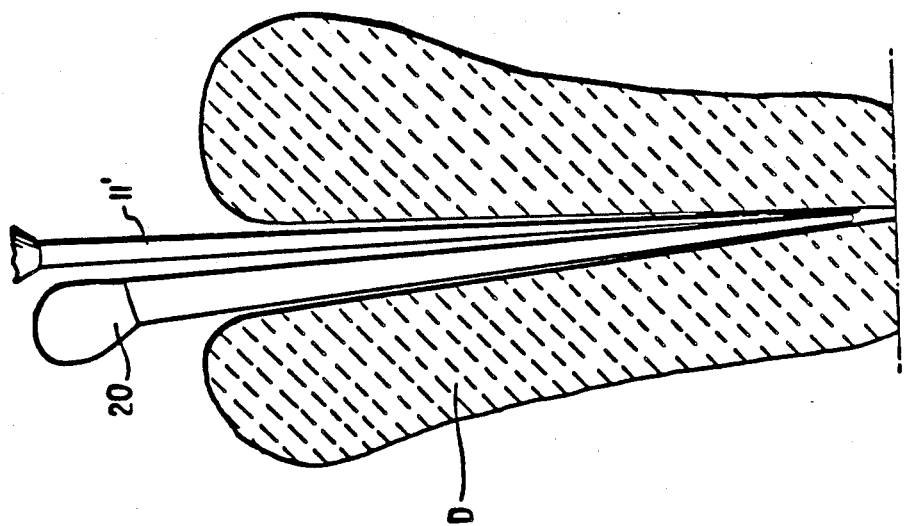

FIGS. 6 and 7 illustrate schematically two successive stages in the third endodontic procedure operation, which is performed according to the present invention. These figures thus depict an approximation of the form in which the canal was placed by the second operation.

For the third operation, use is made of an instrument 11' whose working portion, illustrated, has the form conventionally employed for the gutta-percha compaction instrument. The upper end of the instrument is provided with a shank having the form shown for shank 11 in FIG. 5 and is mounted in the end piece according to the present invention.

In the first phase illustrated in FIG. 6, a stick 20 of gutta-percha is inserted into the prepared canal and the instrument 11' is then introduced into the canal adjacent the lower end of the stick 20. The end piece is operated to cause instrument 11 to undergo oscillating longitudinal movements which force the lower end of stick 20 down into the bottom of the canal and which, due to the frictional rubbing of instrument 11' against stick 20, heats the lower end of the stick and thus softens it. As a result, the ability of the gutta-percha to be compacted so at to completely fill the prepared canal is enhanced.

After this phase has been completed, instrument 11' is withdrawn and a second stick 21 of gutta-percha is introduced, as shown in FIG. 7. Instrument 11' is then reintroduced into the canal so that its tip is in operative association with the lower end of stick 21, and the above-described operation is repeated with respect to stick 21.

This operation can then continue with further sticks until the canal has been completely filled.

While, in the illustrated embodiment fingers 5a are shown as integral with core member 5, it will be appreciated that fingers 5a could alternatively be part of a sleeve inserted into core 5. Such sleeve could then be made of a material, and have a wall thickness, selected to cause fingers 5a to grip an instrument shank with the desired holding force.

It will be understood that the above description of the present invention is susceptible to various modifications, changes and adaptations, and the same are intended to be comprehended within the meaning and range of equivalents of the appended claims.

What is claimed is:

1. Drive head for an endodontic treatment instrument, comprising: a support body provided with a passage; instrument support means having a longitudinal axis and mounted in said passage for movement relative to said body in the direction of said longitudinal axis; and drive means driven to undergo reciprocating movement having at least a component parallel to said longitudinal axis, said drive means being coupled to said instrument support means with play in the direction of said longitudinal axis for imparting to said intrument support means alternating movements having an amplitude which is varible in the direction of said longitudinal axis, said instrument support means constituting means for supporting an endodontic treatment instrument in a manner to cause the instrument to move with said instrument support means in the direction of said longitudinal axis.

2. Drive head as defined in claim 1 wherein said instrument support means comprise a core member for supporting an instrument and having a generally cylindrical form, and said passage in said support body has a cylindrical form dimensioned for guiding said core member.

3. Drive head as defined in claim 2 wherein said core member is provided with a groove extending radially inwardly from its periphery, said drive head further comprises a shaft mounted for rotation relative to said support body and having an axial end face adjacent said core member, and said drive means comprise an eccentric member carried by said shaft at said axial end face thereof and disposed within said groove, said groove and said eccentric member being dimensioned for causing the movement imparted to said eccentric member by rotation of said shaft to impart alternating movements in the direction of said longitudinal axis to said instrument support means.

4. Drive head as defined in claim 3 wherein said groove has a dimension, in the direction of said longitudinal axis, which is greater than the largest transverse dimension of said eccentric member, whereby, in the direction of said longitudinal axis, said eccentric member has a selected amount of play relative to said groove in the direction of said longitudinal axis.

5. Drive head as defined in claim 3 wherein said groove has a length dimension, in a plane perpendicular to said longitudinal axis and in a direction parallel to the periphery to said core member, which is greater than the length, in the same direction, of the region traversed by said eccentric member during rotation of said shaft, for giving said core member a limited freedom of rotation about said longitudinal axis and relative to said support body.

6. Drive head as defined in claim 5 wherein the length dimension of said groove has an angular value, about said longitudinal axis, of less than 180° for limiting the freedom of rotation of said core member about said longitudinal axis.

7. Drive head as defined in claim 1 in combination with an endodontic treatment instrument in the form of a file having, on its outer surface, a spiral crest, and said drive means are coupled to said instrument support means for causing the amplitude of the alternating movements imparted to said instrument support means to have a minimum value corresponding substantially to the pitch of the spiral crest.

8. Drive head as defined in claim 1 wherein the endodontic treatment instrument is provided with a shank for attachment to said instrument support means, and said instrument support means are provided with an axial recess constructed for removably receiving and retaining the shank of such endodontic treatment instrument.

9. Drive head as defined in claim 1 wherein said support body comprises means defining a wall of said passage, said wall extending perpendicular to said longitudinal axis, and further comprising a layer of plastic material disposed on said wall for damping vibrations of said instrument support means.

10. Endodontic treatment apparatus composed of an endodontic treatment instrument in the form of a file having, on its outer surface, a spiral crest, in combination with a drive head, said drive head comprising: a support body provided with a passage; instrument support means having a longitudinal axis and mounted in said passage to undergo movement relative to said body in the direction of said longitudinal axis; drive means for producing alternating movement forces in the direction of said longitudinal axis; and means coupling said drive means to said instrument support means for causing said support means to undergo, in the direction of said longitudinal axis, alternating movements having an amplitude which has a minimum value corresponding substantially to the pitch of the spiral crest of said file, said instrument support means constituting means for supporting said endodontic treatment instrument in a manner to cause said instrument to move with said instrument support means in the direction of said longitudinal axis and to have a freedom of rotation of less than 180° about said longitudinal axis and relative to said support body.

* * * * *